(12) United States Patent
Mukai

(10) Patent No.: US 7,508,043 B2
(45) Date of Patent: Mar. 24, 2009

(54) SENSOR FOR ANALYZING A SAMPLE BY UTILIZING LOCALIZED PLASMON RESONANCE

(75) Inventor: Atsushi Mukai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 288 days.

(21) Appl. No.: 11/224,279

(22) Filed: Sep. 13, 2005

(65) Prior Publication Data
US 2006/0055933 A1 Mar. 16, 2006

(30) Foreign Application Priority Data
Sep. 13, 2004 (JP) ............... 2004/265435

(51) Int. Cl.
*C25D 11/04* (2006.01)
*H01L 31/0236* (2006.01)
*G01N 21/17* (2006.01)

(52) U.S. Cl. ............... 257/428; 257/21; 257/E31.13; 356/445

(58) Field of Classification Search .............. 257/12, 257/14, 21, 252, 253, 428–466, E31.13; 356/445
See application file for complete search history.

(56) References Cited

U.S. PATENT DOCUMENTS 6,541,386 B2 * 4/2003 Aiba et al. .................. 438/707

FOREIGN PATENT DOCUMENTS

| JP | 11-200090 A | 7/1999 |
|---|---|---|
| JP | 2000-356587 A | 12/2000 |
| JP | 2003268592 A | * 9/2003 |

OTHER PUBLICATIONS

Sandrock et al.; Synthesis and Second-Harmonic Generation Studies of Noncentrosymmetric Gold Nanostructures; J. Phys. Chem. B; 1999; vol. 103; No. 14; pp. 2668-2673.*
David D. Goad, "Colloidal metal in aluminum-oxide", J. Appl. Phys., May 1978, pp. 2929-2934, vol. 49, No. 5.
A. Anderson, et al., "Nickel pigmented anodic aluminum oxide for selective absorption of solar energy," J. Appl. Phys., Jan. 1980, pp. 754-764, vol. 51, No. 1.
H. Masuda, "High Regular Metal Nanohole Array", Solid Physics, 1996, pp. 493-498, vol. 31, No. 5.
Hideki Masuda, et al., "Highly ordered nanochannel-array architecture in anodic alumina", Applied Physics, Nov. 10, 1997, pp. 2770-2772, vol. 171, No. 19.

* cited by examiner

*Primary Examiner*—Marcos D. Pizarro
(74) *Attorney, Agent, or Firm*—Sughrue Mion, PLLC

(57) ABSTRACT

A sensor chip for use in a sensor for detecting the localized plasmon resonance state of a metal particle surface by light and analyzing properties of a sample present near metal particles. The sensor chip includes a support with a plurality of pits individually and independently formed in one surface thereof so that they extend toward an interior thereof, and metal particle rods respectively held in the plurality of pits so that an end surface of each rod is exposed at the one surface of the support and a longitudinal side surface of each rod is covered with the support.

5 Claims, 4 Drawing Sheets

SENSOR FOR ANALYZING A SAMPLE BY UTILIZING LOCALIZED PLASMON RESONANCE

BACKGROUND OF THE INVENTION

1. Field of the Invention

The present invention relates to a sensor for detecting the localized plasmon resonance state of a metal particle surface by light and analyzing a sample present near metal particles, a method of analyzing a sample by the use of the sensor, a sensor chip employed in the sensor, and a method of manufacturing the sensor chip.

2. Description of the Related Art

For example, as disclosed in Japanese Unexamined Patent Publication No. 2000-356587, there is known a sensor in which a fine structure, having a layer of metal particles fixed on the surface of a dielectric or semiconductor, etc., is employed as a sensor chip to measure the refractive index, etc., of a sample by making use of localized plasmon resonance. This sensor basically includes means for irradiating measuring light to the metal particles of the sensor chip, and light detection means for detecting the intensity of the measuring light transmitted through or reflected at the metal particle layer.

In the aforementioned sensor, if measuring light is irradiated onto the metal particle layer, localized plasmon resonance takes place at a particular wavelength, and consequently, the scattering and absorption of the measuring light increase appreciably. Therefore, if the sensor is set so the intensity of the measuring light transmitted through or reflected at the metal particle layer can be detected, the occurrence of localized plasmon resonance can be confirmed by observing that the intensity of the detected light attenuates sharply.

The wavelength where localized plasmon resonance takes place, and the degree of the scattering and absorption of measuring light, depend upon the refractive index of a substance present near metal particles. In other words, as the refractive index becomes greater, the resonance peak wavelength shifts to a longer wavelength side and the scattering and absorption of measuring light increase. Therefore, by irradiating measuring light to a metal particle layer with a sample arranged near the metal particle layer and then detecting the intensity of the measuring light transmitted through or reflected at the metal particle layer, the refractive index of the sample and properties of the sample relating to it can be measured.

In this case, by employing white light as measuring light and spectrally detecting the light transmitted through or reflected at the metal particles, the aforementioned resonance peak wavelength shift may be detected. Alternatively, by employing monochromatic light, the aforementioned resonance peak wavelength shift, and a change in the light intensity associated with a change in the scattering and absorption of the measuring light, may also be detected.

In detecting the measuring light transmitted through or reflected at the metal particle layer, the measuring light transmitted through the metal particle layer may be detected by arranging a photodetector on a side opposite to the measuring-light irradiation side with respect to the metal particles, or the measuring light reflected at the metal particles may be detected by arranging the photodetector on the same side as the measuring-light irradiation side with respect to the metal particles. In the latter case, if the substrate for fixing the metal particle layer is formed from a reflective material, the measuring light transmitted through the metal particles is reflected at the substrate and therefore the light transmitted through the metal particles can also be detected.

If a sensing medium to bind with a particular substance is fixed near the metal particles of the sensor chip, the refractive index of the particular substance near the metal particles changes, depending on the presence or absence of the binding between the sensing medium and the particular substance. Hence, by irradiating measuring light to the metal particles with the aforementioned sensing medium fixed near the metal particles and detecting the intensity of the measuring light transmitted through or reflected at the metal particles, it is also possible to detect the presence or absence of the binding between the particular substance and the sensing medium. Note that examples of the particular substance and sensing medium combination are various antigens and an antibody, etc.

A conventional sensor chip used in a sensor making use of the localized plasmon resonance is shown in Japanese Unexamined Patent Publication No. 2000-356587 by way of example. In this sensor chip, a single layer of metal colloid is formed on one surface of a substrate. As also shown in "Colloidal metal in aluminum-oxide", by David G. W. Goad and M. Moskovits, Journal of Applied Physics, Vol. 49, No. 5, pp. 2929-2934, May 1978 and "Nickel pigmented anodic aluminum oxide for selective absorption of solar energy" by A. Andersson, et al., Journal of Applied Physics, Vol. 51, No. 1, pp. 754-764, January 1980, a sensor chip comprises an anodic alumina layer with a plurality of pits in one surface thereof, and metal particles with which the pits are filled up. This sensor chip can also be used in the aforementioned sensor. In the conventional sensor chips, the aforementioned metal particles comprise metal particles in the form of lumps, having nearly the same three-dimensional dimensions. Examples of the anodic alumina layer with a plurality of pits are also disclosed in Japanese Unexamined Patent Publication. No. 11 (1999)-200090 and "High Regular Metal Nanohole Array," by H. Masuda, Solid Physics, Vol. 31, No. 5, pp. 493-498, 1996.

Incidentally, if a sample is to be analyzed by the sensor making use of the localized plasmon resonance, a change in the resonance peak wavelength and a change in the intensity of the measuring light must be detected before and after the supply of the sample to the metal particle layer, as described above. The resonance peak wavelength and the intensity of the measuring light will change even if the incidence angle of the measuring light with respect to the metal particle layer changes. Hence, the incidence angles need to coincide before and after the supply of the sample to the metal particle layer. For that reason, throughout the time from when a sample is supplied to the metal particle layer to when an analysis of the sample is completed, the sensor chip is fixed to prevent the occurrence of a shift in the sensor chip that will cause a shift in the incidence angle.

However, particularly in the case where the presence or absence of the aforementioned sensing medium and particular substance binding is judged, the sensing chip has to be fixed for a long period of time until the reaction between them starts and is completed. Thus, during the time the sensor chip is fixed, that is, until the aforementioned reaction is completed, it is impossible to use the sensor to analyze another sample. Because of the waiting time, the efficiency of sample analysis is decreased.

SUMMARY OF THE INVENTION

The present invention has been made in view of the aforementioned circumstances. Accordingly, an aspect of the present invention provides a sensor in which there is no possibility that the efficiency of sample analysis will be reduced by fixing a sensor chip for a long period of time, and a method of analyzing a sample by the use of the sensor. Another aspect of the invention provides a sensor chip employed in the aforementioned sensor and a method of manufacturing the sensor chip.

In accordance with the present invention, there is provided a sensor chip for use in a sensor for detecting a localized plasmon resonance state of a metal particle surface and analyzing properties of a sample present near metal particles. The sensor chip of the present invention comprises two major components: (1) a support with a plurality of pits individually and independently formed in one surface thereof so that they extend toward an interior thereof; and (2) rods of metal particles, whose aspect ratio (the ratio between diameter and length) is not 1, respectively held in the plurality of pits so that an end surface of each rod is exposed at the one surface of the support and a longitudinal side surface of each rod is covered with the support.

In accordance with the present invention, there is provided a method of manufacturing the sensor chip of the present invention. The method comprises the steps of (a) forming on one surface of a support an anodic alumina layer having a plurality of through pits extending in a direction substantially perpendicular to the one surface; (b) forming in the one surface of the support a plurality of pits corresponding to the through pits and extending in the direction of the depth of the support, by etching the support with the anodic alumina layer as a mask; (c) removing the anodic alumina layer; and (d) filling up the pits of the support with rods of metal particles respectively, by depositing metal particles on the one surface of the support and within the pits and then removing the metal particles deposited on the one surface.

In accordance with the present invention, there is provided a first sensor employing the sensor chip of the present invention described above. The first sensor comprises five major components: (1) means for irradiating measuring light having a predetermined wavelength band to the rods of metal particles of the sensor chip; (2) sensor-chip hold means for holding the sensor chip so that the longitudinal axes of the metal particle rods are inclined with respect to an electric field direction of the measuring light, and so that the angle of inclination can be freely changed; (3) drive means for driving the sensor-chip hold means so that the angle of inclination is changed; (4) light detection means for spectrally detecting an intensity of the measuring light transmitted through the metal particle rods or reflected at the metal particle rods; and (5) control means for setting a direction of the sensor-chip hold means so that the angle of inclination is fixed, by controlling operation of the drive means based on the intensity detected by the light detection means.

In accordance with the present invention, there is provided a second sensor employing the sensor chip of the present invention described above. The second sensor comprises four major components: (1) means for irradiating measuring light having a predetermined wavelength band to the rods of metal particles of the sensor chip; (2) sensor-chip hold means for holding the sensor chip so that the longitudinal axes of the metal particle rods are inclined with respect to an electric field direction of the measuring light, and so that the angle of inclination can be freely changed; (3) light detection means for spectrally detecting an intensity of the measuring light transmitted through the metal particle rods or reflected at the metal particle rods; and (4) display means for displaying the intensity detected by the light detection means.

In accordance with the present invention, there is provided a method of analyzing a sample by employing the aforementioned second sensor. The method comprises the steps of: (a) irradiating measuring light to the metal particles of the sensor chip before and after the sample is supplied; (b) storing an intensity of the measuring light measured at a first particular wavelength of a wavelength band of the measuring light, displayed on the display means when the measuring light is irradiated before sample supply; (c) adjusting an angle of inclination of the sensor chip held by the sensor-chip hold means so that an intensity of the measuring light at the first particular wavelength, displayed on the display means after sample supply, coincides with the stored intensity; and (d) analyzing the sample, based on the intensity of the measuring light measured at a second particular wavelength different from the first particular wavelength, displayed on the display means.

BRIEF DESCRIPTION OF THE DRAWINGS

The present invention will be described in further detail with reference to the accompanying drawings wherein:

FIG. 2, which includes

FIG. 5, which includes

DESCRIPTION OF THE PREFERRED EMBODIMENTS

Figure 1:
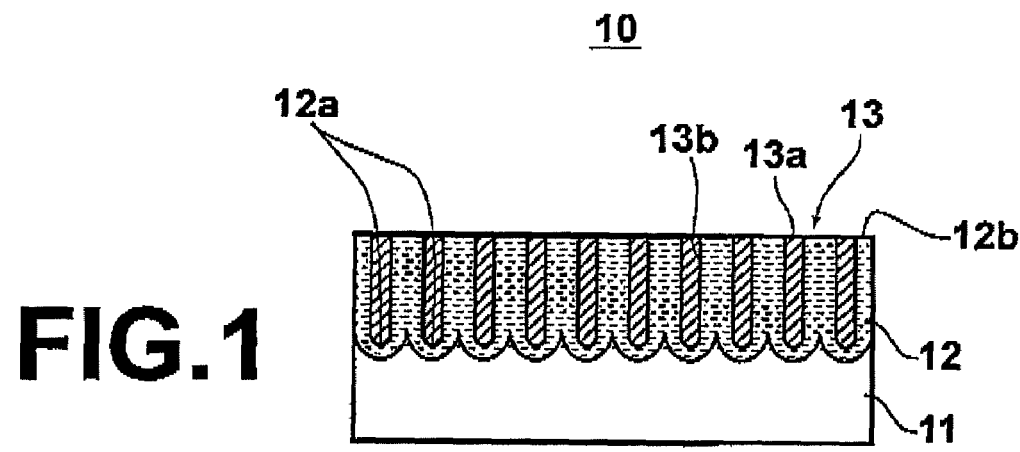
FIG. 1 is a schematic side view showing a sensor chip constructed in accordance with a first embodiment of the present invention.

Referring initially to FIG. 1, there is shown a sensor chip 10 constructed in accordance with a first embodiment of the present invention. The sensor chip 10 shown in the figure comprises a layer of anodic alumina 12 as a support formed on an aluminum substrate 11, and gold particles 13 with which a great number of pits 12a formed in one surface of the anodic alumina 12 are filled up.

In the sensor chip 10, the depth of each pit 12a is about 200 nm or less as an example and the inside diameter is, for example, about a few nm to 100 nm. Since the gold particles 13 are held in the pits 12a, they are shaped as elongated rods. The end surface 13a of each gold particle rod 13 is exposed at the one surface 12b of the anodic alumina 12, while the longitudinal side surface 13b is covered with the anodic alumina 12.

Figure 2A:
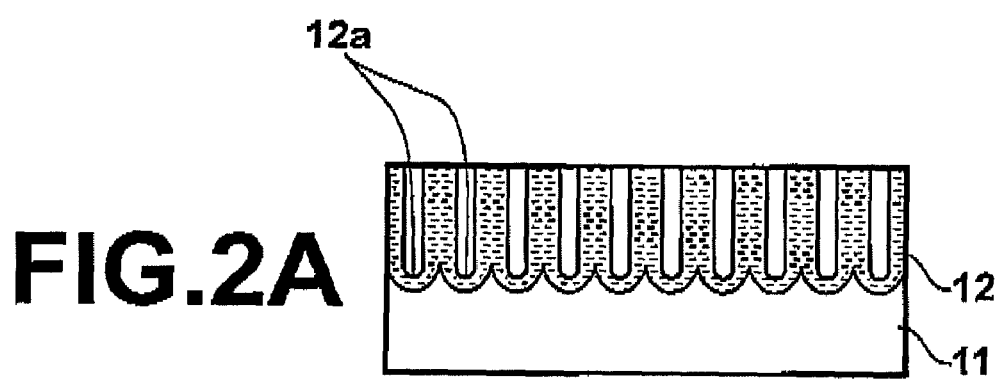
FIGS. 2A and 2B, is a simplified diagram used to explain a method of manufacturing the sensor chip shown in FIG. 1.
Figure 2B:
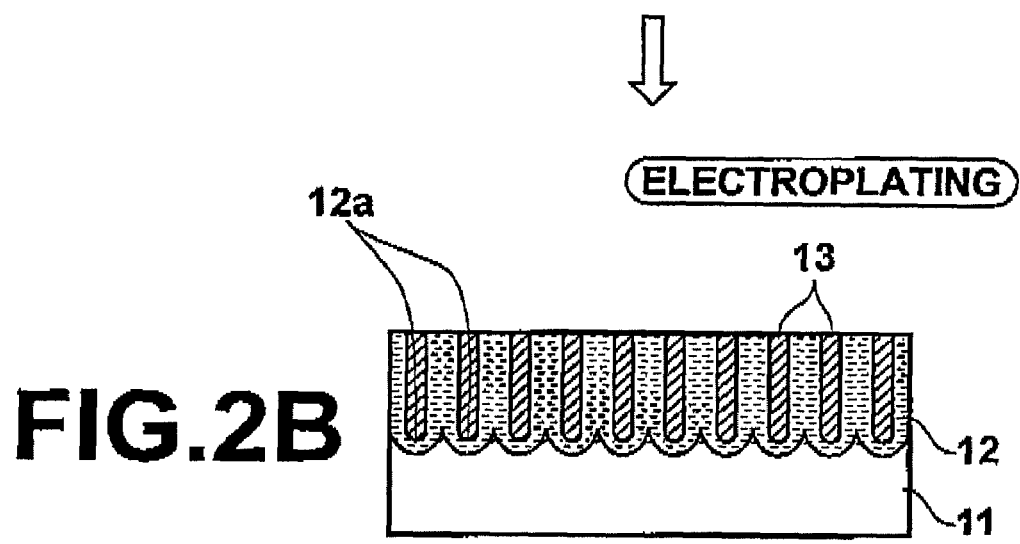

Referring now to FIG. 2, there is shown a method of manufacturing the aforementioned sensor chip 10. As shown in FIG. 2A, an aluminum substrate 11 with a layer of anodic alumina 12 formed on the surface is first prepared. Then, one surface 12b of the anodic alumina 12 layer in which pits 12a are formed is electroplated with gold. As a result, as shown in FIG. 2B, the pits 12a in the anodic alumina 12 are filled up with gold particles 13. If electroplating conditions are suitably controlled, only pits 12a can be filled up with gold particles 13, without plating the surface 12b of the anodic alumina 12 with gold. Instead of electroplating, the pits 12a can also be filled up with gold particles 13 by vapor deposition.

Note that instead of the gold particle rods 13, metal particle rods may be formed from other metals such as silver, copper, aluminum, etc. However, in forming the sensor chip 10 of the present invention, gold is the particularly preferred material in view of the following points. That is, because gold is malleable and ductile, vapor deposition can be easily performed even at relatively low temperatures. Gold is also high in corrosion resistance. Therefore, when the sensor chip 10 is used in a sensor to be described later, the sensor is able to have stable properties. The sensor is also made easier to handle when manufactured and used.

Now, a method of forming the anodic alumina layer 12 on the aluminum substrate 11 will be described. Although there are various methods, a method of simultaneously advancing generation of an oxide film and dissolution of the generated oxide layer is basically employed in performing an anodic oxidation process on the aluminum substrate 11 in an acid electrolytic solution. According to this method, pits are randomly formed in the surface of an oxide layer formed on the aluminum substrate 11 at the start of the anodic oxidation, by dissolution action by acid. With the progress of the anodic oxidation, some of the pits grow preferentially and are arranged at nearly equal intervals. Because an electric field applied to the pitted portion in the oxide film is higher than that applied to the non-pitted portion, dissolution of the pitted portion is more easily expedited. As a result, in the anodic alumina layer 12, pits 12a are selectively formed with the growth, while an undissolved portion is formed so as to surround the pits 12a.

In the anodic alumina 12 thus obtained, a great number of pits 12a are regularly arranged and formed. These pits 12a extend in a direction approximately perpendicular to the surface of the anodic alumina 12 and respectively form cylindrical spaces that are nearly the same in cross section and closed at the bottoms.

Note that Japanese Unexamined Patent Publication Nos. 2001-9800 and 2001-138300 disclose methods of controlling the positions at which the aforementioned pits are formed. In these methods, dissolution-starting points are formed at the desired positions, for example, by irradiating a focused ion beam to aluminum. After this process, by performing an anodic oxidation process, pits 12a can be formed at the desired positions. And in irradiating the focused ion beam, if the irradiation quantity, beam diameter, irradiation energy, etc., are controlled, the indentation and composition of the dissolution-starting point can be varied. Therefore, the diameter of each pit 12a to be finally formed can also be freely controlled.

As an example of a method of arranging the pits 12a at high density, there is a method employing oxalic acid. That is, by employing oxalic acid as an electrolytic solution for anodic oxidation and performing an anodic oxidation process under a constant voltage of about 40 V, pits 12a can be regularly arranged at high density. Because the regular arrangement of the pits 12a progresses with the lapse of anodic oxidation time, the pits 12a can be regularly arranged at high density by performing the anodic oxidation process for a long period of time.

Since the diameter, pitch, and depth of the pits 12a can be relatively freely controlled in the aforementioned manner, gold particles 13 can be formed to an arbitrary uniform size and it becomes possible to arrange them regularly. As a result, if the sensor chip 10 is employed in a sensor described later, the sensitivity can be enhanced and stabilized.

Figure 3:
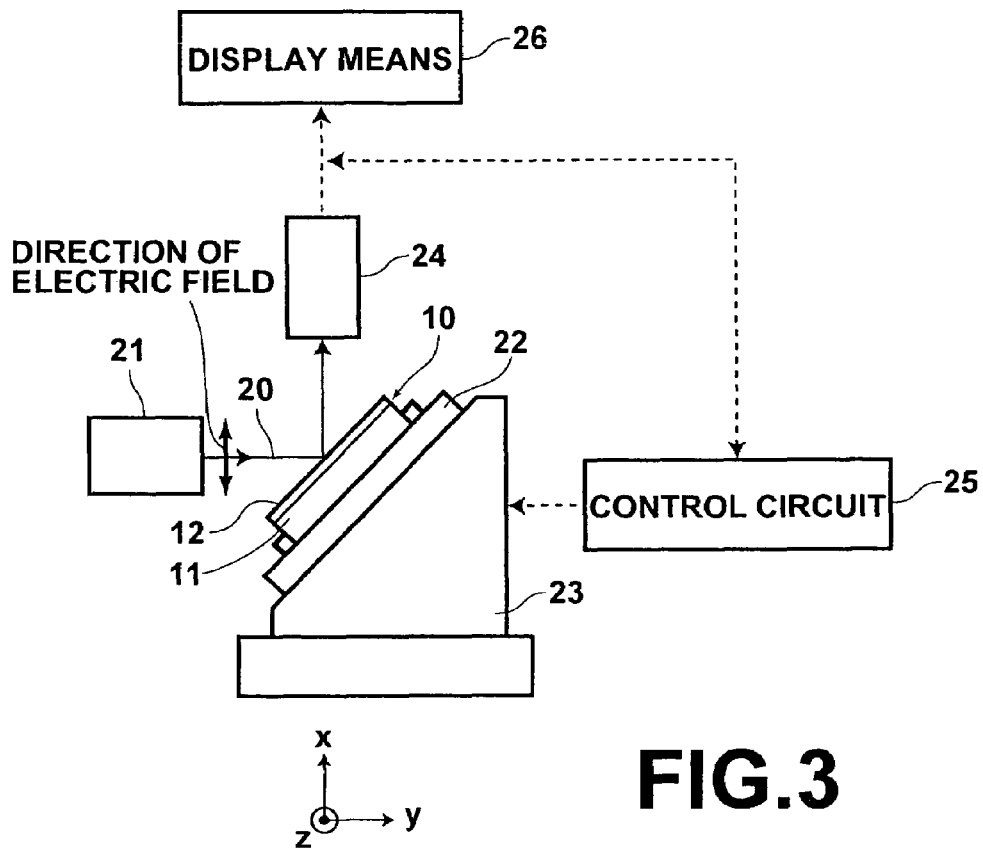
FIG. 3 is a schematic side view showing a sensor including the sensor chip shown in FIG. 1.

Referring now to FIG. 3, there is shown a sensor employing the aforementioned sensor chip 10. As shown in the figure, this sensor comprises six major components: (1) a white light source 21 for irradiating measuring light 20 (e.g., white light) to the gold particle rods 13 of the sensor chip 10; (2) sensor-chip hold means 22 for holding the sensor chip 10 so that the longitudinal axis of each gold particle rod 13 is inclined with respect to the electric field direction of the measuring light 20; (3) a three-axis revolvable actuator 23 for fixing the sensor-chip hold means 22 thereto; (4) a polychromator 24 for spectrally detecting the intensity of the measuring light 20 reflected at the gold particles 13; (5) a control circuit 25 for controlling operation of the actuator 23 based on the intensity measured by the polychromator 24; and (6) display means 26 connected to the control circuit 25 and polychromator 24.

With the anodic alumina 12 upward, the sensor chip 10 is arranged on the sensor-chip hold means 22. The three-axis revolvable actuator 23 can cause the sensor-chip hold means 22 to revolve on x, y, and z axes shown in FIG. 3. In this manner, the sensor-chip hold means 22 can change in posture. If the posture of the sensor-chip hold means 22 is changed, the angle of inclination of each gold particle rod 13 changes accordingly.

If the measuring light 20 (which is white light) is irradiated onto the sensor chip 10, it is reflected at the gold particles 13 (see FIG. 1). The reflected light 20 is detected by polychromator 24. Typically, the spectral intensity characteristic of the reflected light is represented by a solid line shown in FIG. 4. That is, when the measuring light 20 is irradiated onto the gold particles 13 of the anodic alumina 12, absorption of the measuring light 20 is increased at particular wavelengths $\lambda 1$ and $\lambda 2$ by localized plasmon resonance. Note that the solid line in FIG. 4 represents absorbance of the measuring light 20 reflected at the anodic alumina 12 before sample supply.

The wavelengths (resonance peak wavelengths) at which localized plasmon resonance occurs, and the degree of absorption (absorbance) of the measuring light 20, depend upon the refractive index of a substance present around the gold particles 13. That is, as the refractive index becomes greater, the resonance peak wavelength is shifted to a longer wavelength side and the absorbance increases.

Figure 4:
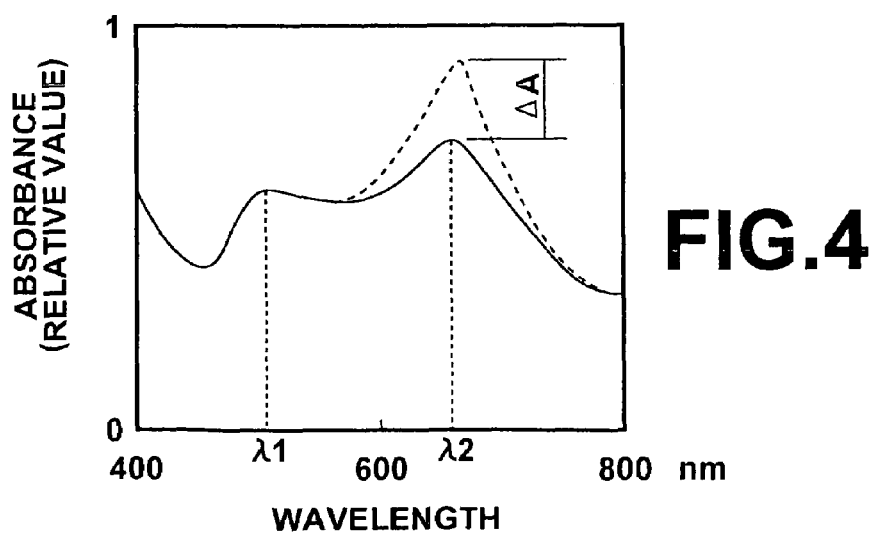
FIG. 4 is a graph showing the spectral intensity characteristic of the measuring light detected by the sensor shown in FIG. 3.

The first resonance peak wavelength $\lambda 1$ shown in FIG. 4 depends on the side surface 13b of each gold particle rod 13, while the second resonance peak wavelength $\lambda 2$ depends on the end surface 13a of the gold particle rod 13. Therefore, if a sample is supplied to the anodic alumina 12, the second resonance peak wavelength $\lambda 2$ is shifted as described above and the absorbance at that wavelength increases by $\Delta A$. The spectral absorption characteristic varies as shown by the broken line in FIG. 4. The reason is that if a sample is supplied, it adheres to the end surface 13a of each gold particle rod 13 and the refractive index of the substance in contact with the end surface 13a changes.

On the other hand, since the supplied sample does not adhere to the side surface 13b of each gold particle rod 13, the first resonance peak wavelength $\lambda 1$ is not shifted and the absorbance at that wavelength does not increase. Therefore, if the first resonance peak wavelength $\lambda 1$ is shifted or the absorbance at that wavelength increases, the shift or increase is considered to be due to a shift in the angle of inclination of the sensor chip 10 with respect to the measuring light 20.

In the foregoing description, a sample is supplied to the gold particles 13 of the sensor chip 10. Similarly, even in the case where the aforementioned sensing medium (e.g., one of between an antigen and an antibody) is fixed on the gold particle rods 13 and it is detected whether a particular substance (e.g., the other of the two) as a sample binds to the sensing medium, the refractive index of the medium in contact with the end surface 13a of each gold particle rod 13 changes due to the binding, while the side surface 13b of each gold particle rod does not cause any change in the refractive index of the medium. Thus, circumstances are similar to the aforementioned case.

In the sensor shown in FIG. 3, samples are analyzed by making use of the aforementioned principles and a shift in the inclination angle of the sensor chip 10 is prevented from occurring before and after sample supply. These points will hereinafter be described in detail.

The control circuit 25 receives a signal from the polychromator 24 that has detected the intensity of the measuring light 20 reflected at the gold particle rods 13 of the sensor chip 10, and then calculates the absorbance characteristic shown in FIG. 4. For the longer resonance peak wavelength $\lambda$ 2 of the two resonance peak wavelengths, the control circuit 25 detects a shift in the resonance peak wavelength and an increase in the absorbance after sample supply. Based on the wavelength shift and absorbance increase, the control circuit 25 calculates the refractive index of the sample and properties relating to it and displays them on the display means 26.

For the shorter resonance peak wavelength $\lambda$ 1 of the aforementioned two resonance peak wavelengths, the control circuit 25 calculates the absorbance at that wavelength before sample supply and stores the calculated value in storage means (not shown). For example, if a sensor-chip angle alignment command is input through input means such as a keyboard (not shown) after a sample is supplied to the sensor chip 10, operation of the three-axis revolvable actuator 23 is controlled so that the absorbance at the first resonance peak wavelength $\lambda$ 1 measured at the time of the sample supply coincides with the absorbance previously stored in the storage means (not shown). In this manner, if the measured value of the absorbance at the first resonance peak wavelength $\lambda$ 1 coincides with the value of the stored absorbance, the angle of inclination of the sensor chip 10 with respect to the measuring light 20 (i.e., the inclination angle of the gold particle rods 13) coincides with the inclination angle arranged before sample supply.

Thus, after the inclination angle of the sensor chip 10 with respect to the measuring light 20 coincides with the inclination angle arranged before sample supply, the sample is analyzed based on the shift in the resonance peak wavelength $\lambda$ 2 and increase in the absorbance. Therefore, since there is no possibility that errors in measurement will be caused by a shift in the inclination angle of the sensor chip 10, accuracy in sample analysis can be enhanced.

As described above, if it is possible to cause the inclination angle of the sensor chip 10 to coincide with the inclination angle arranged before sample supply by inputting a sensor-chip angle alignment command to the control circuit 25, it becomes unnecessary to fix the sensor chip 10 to the sensor-chip hold means 22 to prevent a shift in the inclination angle of the sensor chip 10 throughout the time from when a sample is supplied to the sensor chip 10 to when the sample analysis is completed. That is, if the sensor chip 10 is set to the sensor-chip hold means 22 and the spectral absorption characteristic before sample supply, shown by a solid line in FIG. 4, is obtained, there is no problem, even if the sensor chip 10 is removed from the sensor-chip hold means 22 until the aforementioned resonance peak wavelength shift and absorbance increase are next measured.

Therefore, particularly in the case of detecting the presence or absence of an antigen-antibody reaction, it is also possible to remove the sensor chip 10 from the senor-chip hold means 22 for relatively long periods of time required for the reaction to progress and cause the reaction to progress outside the sensor. If so, another sample can be analyzed by setting another sensor chip 10 to the sensor-chip hold means 22. Thus, the efficiency of sample analysis is considerably enhanced.

In the aforementioned sensor, the inclination angle of the sensor chip 10 is automatically adjusted by the three-axis revolvable actuator 23 and control circuit 25 so that the absorbance at the first resonance peak wavelength $\lambda$ 1, measured at the time of the input of a sensor-chip angle alignment command, coincides with the value of the absorbance previously stored. It is also possible to perform a sensor-chip angle adjustment by hand. In that case, an actuator capable of being operated by hand is used as the three-axis revolvable actuator 23. In addition, the absorbance characteristic shown in FIG. 4 is displayed on the display means 26, and the absorbance at the first resonance peak wavelength $\lambda$ 1 before sample supply, displayed on the display means 26, is stored. After sample supply, the three-axis revolvable actuator 23 is manually operated so that the absorbance at the first resonance peak wavelength $\lambda$ 1 displayed on the display means 26 coincides with the stored absorbance. Alternatively, instead of employing the three-axis revolvable actuator 23 capable of being operated manually and mechanically, the sensor-chip hold means 22 may be operated by drive means capable of being operated only by hand.

Figure 5A:
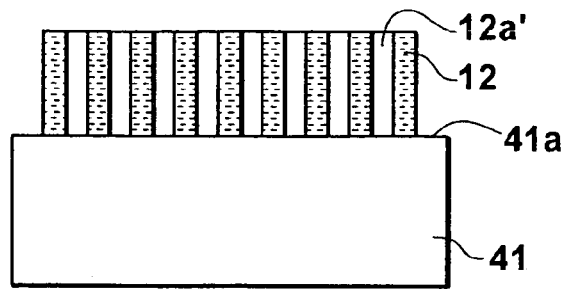
FIGS. 5A to 5E, is a schematic side view showing how a sensor chip is manufactured in accordance with a second embodiment of the present invention.

In addition to being formed from anodic alumina, the support of the sensor chip of the present invention can also be formed by other methods. For example, in FIG. 5, there is shown a sensor chip manufactured in accordance with a second embodiment of the present invention. As shown in FIG. 5A, on one surface 41a of a transparent dielectric substrate 41 formed from polystyrene, etc., there is provided an anodic alumina layer 12 having a plurality of through pits 12a' extending in a direction substantially perpendicular to the one surface 41a. Note that the anodic alumina layer 12 shown in FIG. 5 can also be obtained, for example, by removing from the sensor chip 10 shown in FIG. 2 the boundary portion between the aluminum substrate 11 and the anodic alumina layer 12.

Figure 5B:
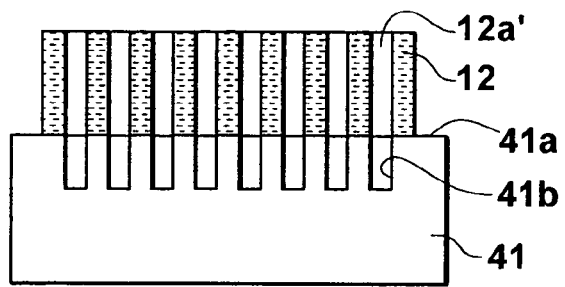

As shown in FIG. 5B, by etching the transparent dielectric substrate 41 with the anodic alumina layer 12 as a mask, a plurality of pits 41b corresponding to the through pits 12a' are formed in the transparent dielectric substrate 41 and extend in the direction of the depth of the transparent dielectric substrate 41. This etching process is performed by employing oxygen or $CF_4$ as an etchant.

Figure 5C:
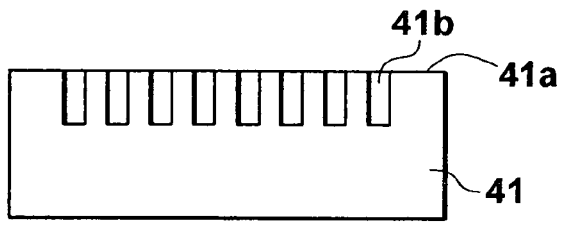
Figure 5D:
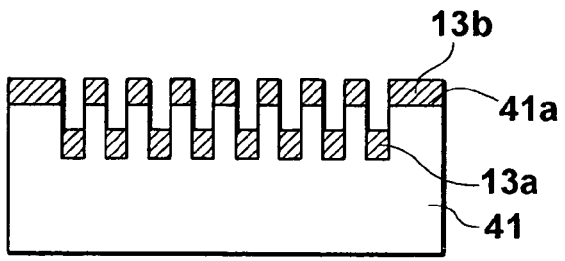

As shown in FIG. 5C, the anodic alumina 12 used as the mask is removed from the transparent substrate 41. As shown in FIG. 5D, the one surface 41a of the transparent dielectric substrate 41 is covered with gold by vapor deposition or sputtering. As a result, gold particles 13b are deposited on the one surface 41a of the transparent dielectric substrate 41 and gold particles 13a are deposited within the pits 41b of the transparent dielectric substrate 41.

Figure 5E:
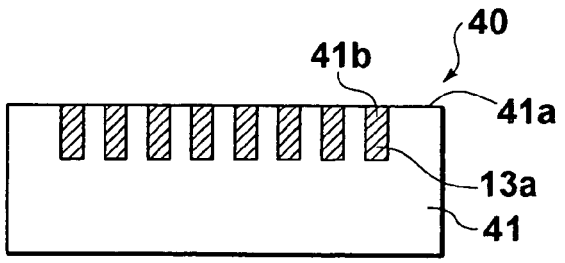

After the pits 41b are filled up with gold particles 13a, the gold particles 13b on the one surface 41a of the transparent dielectric substrate 41 are removed as shown in FIG. 5E. As a result, a sensor chip 40 with the pits 41b respectively filled up with gold particle rods 13a is obtained.

The sensor chip 40 can be a component of the sensor of the present invention, as with the sensor chip 10 shown in FIG. 1. In addition, because the support of the sensor chip 40 is formed from the transparent dielectric substrate 41, it is also possible to analyze a sample by irradiating measuring light to the gold particle rods 13 and detecting the measuring light transmitted through the sensor chip 40.

Figure 6:
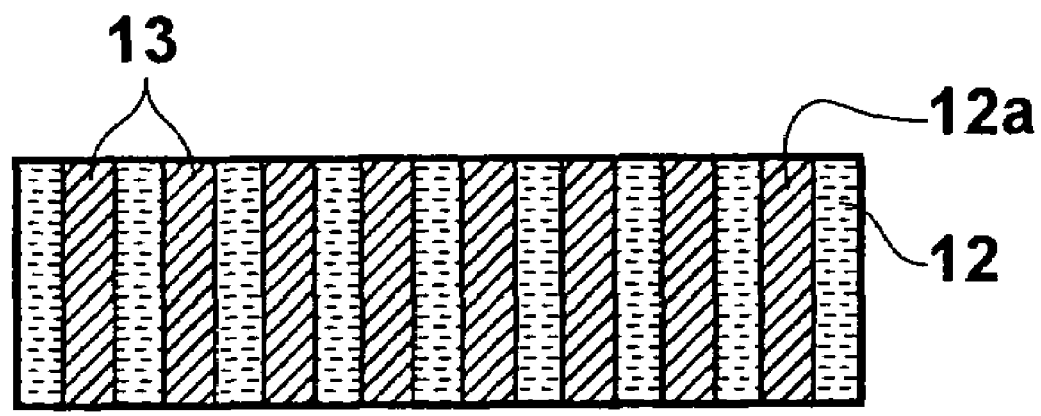
FIG. 6 is a schematic side view showing a sensor chip constructed in accordance with a third embodiment of the present invention.

Finally, referring to FIG. 6, there is shown a sensor chip 50 constructed in accordance with a third embodiment of the present invention. This sensor chip 50 is manufactured by employing the anodic alumina layer 12 with through pits 12a' which is used in manufacturing the sensor chip 40 shown in FIG. 5. That is, if the through pits 12a in the anodic alumina layer 12 are filled up with gold particles 13, the sensor chip 50 is obtained. Because measuring light is transmitted through the anodic alumina layer 12 of the sensor chip 50, it is also possible to analyze a sample by detecting the measuring light transmitted through the sensor chip 50.

While the present invention has been described with reference to the preferred embodiments thereof, the invention is not to be limited to the details given herein, but may be modified within the scope of the invention hereinafter claimed.

In the sensor chip of the present invention, as set forth above, a plurality of rods of metal particles whose aspect ratio is not 1 are formed so that an end surface of each rod is exposed at one surface of the support and a longitudinal side surface of each rod is covered with the support. If measuring light is irradiated onto the thus-constructed sensor chip so that an electric field direction thereof is inclined with respect to the longitudinal axis of each rod, and an absorption spectrum from the sensor chip is examined, a first absorption peak depending on the end surface of the metal particle rod and a second absorption peak depending on the side surface of the metal particle rod occur at different wavelengths, because the measuring light is irradiated onto both the end surface and the side surface.

That is, for example, when measuring light is irradiated onto a rod of metal particles in which the diameter is longer than the length, localized plasmon resonance takes place only at a longer wavelength side (e.g., wavelength $\lambda 2$ shown in FIG. 4 described later) if the electric field direction of the measuring light (i.e., the direction of the electric field vector) coincides with the direction of the longitudinal axis of the metal particle rod, and localized plasmon resonance takes place only at a shorter wavelength side (e.g., wavelength $\lambda 1$ shown in FIG. 4) if the electric field direction of the measuring light coincides with the direction of the diameter of the metal particle rod. However, if measuring light is irradiated with the electric field direction inclined with respect to the longitudinal axis of the metal particle rod, localized plasmon resonance occurs at both the aforementioned longer wavelength side and shorter wavelength side. Note that the difference between the wavelengths $\lambda 1$ and $\lambda 2$ becomes greater as the aspect ratio of the metal particle rod becomes greater away from 1. In the case where the aspect ratio is 1, the two wavelengths coincide. Therefore, it is vital to employ a rod of metal particles whose aspect ratio is not 1.

When the electric field direction of measuring light is coincident with the direction of the longitudinal axis of a metal particle rod, the wavelengths at which localized plasmon resonance takes place are determined according to the boundary conditions of the interface between the metal particle rod in the longitudinal axis direction and the surrounding medium and to the length of the metal particle rod. The aforementioned "absorption peak depending on the end surface of a metal particle rod" indicates an absorption peak occurring in this case. On the other hand, when the electric field direction of measuring light is coincident with the direction of the diameter of a metal particle rod, the wavelengths at which localized plasmon resonance takes place are determined according to the boundary conditions of the interface between the metal particle rod in the diameter direction and the surrounding medium and to the diameter of the metal particle rod. The aforementioned "absorption peak depending on the side surface of a metal particle rod" indicates an absorption peak occurring in this case.

The end surface of a metal particle rod is exposed at one surface of the support, while the side surface is covered with the support. For this reason, a sample adheres to the rod end surface, but it cannot adhere to the side surface. Therefore, the absorption peak depending on the end surface of a metal particle rod changes before and after sample supply, and based on the change, the refractive index of the sample and properties relating to it can be analyzed. On the contrary, the absorption peak depending on the side surface does not change before and after sample supply.

Hence, in the sample analysis method of the present invention employing the aforementioned first sensor, if the angle of inclination of the sensor chip by the sensor-chip hold means is adjusted so that the intensity of measuring light at the first particular wavelength (at which the absorption peak depending on the side surface of a metal particle rod takes place), displayed on the display means when the measuring light is irradiated after sample supply, coincides with the stored intensity (i.e., the intensity of the measuring light at the first particular wavelength displayed on the display means when the measuring light is irradiated before sample supply), then the inclination angles coincide before and after sample supply.

Thus, if it is possible to cause the angles of inclination of the sensor chip to coincide before and after sample supply, it becomes unnecessary to fix the sensor chip to the sensor-chip hold means throughout the time from the start of the reaction between a sensing medium and a particular substance to the completion of the reaction. During the progress of the reaction, the sensor chip can be removed from the sensor-chip hold means. Therefore, while the sensor chip is removed from the sensor-chip hold means, it becomes possible to perform some or all of sample-analyzing operations with another sensor chip. Thus, the efficiency of sample analysis is considerably enhanced.

Even when the senor-chip hold means is not adjusted so that the angles of inclination of the sensor chip coincide before and after sample supply, errors caused by the inclination of the sensor chip can be removed by detecting the intensity of measuring light at the first and second particular wavelengths before and after sample supply, correcting a measuring-light intensity detection signal detected after sample supply so that the intensities of the measuring light at the first particular wavelength coincide before and after sample supply, and calculating the intensity of the measuring light for the second particular wavelength from the corrected detection signal.

While the sample analysis method employing the second sensor of the present invention has been described, the first sensor of the present invention can automatically carry out the same operations as the aforementioned sample analysis method, because it is equipped with control means for setting the direction of the sensor-chip hold means so that the angle of inclination of the longitudinal axis of the metal particle rod with respect to the electric field direction of the measuring light is fixed.

In the sensor chip of the present invention, as previously mentioned, a plurality of rods of metal particles are provided so that the end surface of each rod is exposed at one surface of the support and the longitudinal side surface is covered with the support. Therefore, the sensor chip of the present invention can constitute the first or second sensor of the present invention.

The aforementioned anodic alumina is formed as a metal oxide layer in the surface of aluminum by performing an anodic oxidation process on the aluminum in an acid electrolytic solution. In this anodic alumina layer, pits of about a few nanometers to a few hundred nanometers in diameter are individually and independently formed so that they extend in a direction substantially perpendicular to the surface. They are also arranged at nearly equal intervals. And the diameter, depth, and pitch of the pits can be relatively freely set by controlling anodic oxidation conditions (see the aforementioned "High Regular Metal Nanohole Array," by H. Masuda, Solid Physics, Vol. 31, No. 5, pp. 493-498, 1996). Since the sensor chip of the present invention is equipped with a plurality of metal particle rods, it is necessary to accurately control the depth of the pits of the support that are to be filled up with the metal particle rods. Hence, the anodic alumina having the aforementioned properties is extremely preferable as the material of the support constituting this sensor chip.

The aforementioned anodic alumina may be employed as a layer formed on the surface of an aluminum substrate, or after being removed from the aluminum surface, it may be fixed on another substrate and employed.

In the sensor chip of the present invention, when forming the support from anodic alumina, the support with a great number of pits can be very easily fabricated and thus a reduction in cost of the sensor chip can be realized.

In the method of manufacturing the sensor chip according to the present invention, on one surface of the support there is provided an anodic alumina layer having a plurality of through pits extending in a direction substantially perpendicular to the one surface. And in the one surface of the support, there are formed a plurality of pits corresponding to the through pits and extending in the direction of the depth of the support, by etching the support with the anodic alumina layer as a mask. Therefore, the pits can be easily formed and the sensor chip can be efficiently manufactured.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as being illustrative and not restrictive, the scope of the invention being indicated by the appended claims, rather than the foregoing description, and all changes which come within the meaning and range of equivalency of the claims are therefore intended to be embraced therein.

For example, in the sensor chip of the present invention, the aforementioned support may be formed from anodic alumina. Also, the aforementioned pits may be formed in the support by an etching process in which anodic alumina with a plurality of pits is used as a mask.

In the sensor chip of the present invention, the maximum dimension of the aforementioned metal particles may be 200 nm or less. The metal particles may be formed from one of among gold, silver, copper, and aluminum.

What is claimed is:

1. A sensor for detecting a localized plasmon resonance state of a metal particle surface by light and analyzing properties of a sample present near metal particles employing a sensor chip, comprising:

means for irradiating measuring light having a predetermined wavelength band to the rods of metal particles of said sensor chip;

sensor-chip hold means for holding said sensor chip so that the longitudinal axes of said metal particle rods are inclined with respect to an electric field direction of said measuring light, and so that the angle of inclination can be freely changed;

drive means for driving said sensor-chip hold means so that said angle of inclination is changed;

light detection means for spectrally detecting an intensity of said measuring light transmitted through said metal particle rods or reflected at said metal particle rods; and control means for setting a direction of said sensor-chip hold means so that said angle of inclination is fixed, by controlling operation of said drive means based on said intensity detected by said light detection means;

wherein the sensor chip comprises:

a support with a plurality of pits individually and independently formed in one surface thereof so that they extend toward an interior thereof; and a plurality of rods of metal particles, whose aspect ratio is not 1, respectively held in said plurality of pits so that an end surface of each rod is exposed at said one surface of said support and a longitudinal side surface of each rod is covered with said support.

2. The sensor as set forth in claim 1, wherein said support is formed from anodic alumina.

3. The sensor as set forth in claim 1, wherein said pits are formed in said support by an etching process in which anodic alumina with a plurality of pits is used as a mask.

4. The sensor as set forth in claim 1, wherein the maximum dimension of said metal particles is 200 nm or less.

5. The sensor as set forth in claim 1, wherein said metal particles are formed from one of among gold, silver, copper, and aluminum.

* * * * *